(12) United States Patent
Aylsworth et al.

(10) Patent No.: US 7,150,280 B2
(45) Date of Patent: *Dec. 19, 2006

(54) METHOD AND SYSTEM FOR DELIVERY OF THERAPEUTIC GAS TO A PATIENT AND FOR FILLING A CYLINDER

(75) Inventors: Alonzo C. Aylsworth, Wildwood, MO (US); Lawrence C. Spector, Austin, TX (US)

(73) Assignee: Acoba, LLC, Chesterfield, MO (US)

( * ) Notice: Subject to any disclaimer, the term of this patent is extended or adjusted under 35 U.S.C. 154(b) by 1 day.

This patent is subject to a terminal disclaimer.

(21) Appl. No.: 11/070,571

(22) Filed: Mar. 2, 2005

(65) Prior Publication Data
US 2005/0145248 A1    Jul. 7, 2005

Related U.S. Application Data

(63) Continuation of application No. 10/636,055, filed on Aug. 7, 2003, now Pat. No. 6,904,913.

(60) Provisional application No. 60/421,375, filed on Oct. 24, 2002.

(51) Int. Cl.
*A61M 16/00* (2006.01)

(52) U.S. Cl. .................. 128/204.22; 128/204.18

(58) Field of Classification Search ........... 128/201.21, 128/204.18, 204.21, 204.22
See application file for complete search history.

(56) References Cited

U.S. PATENT DOCUMENTS

| | | | |
|---|---|---|---|
| 4,215,681 A * | 8/1980 | Zalkin et al. ........ 128/204.21 |
| 4,428,372 A | 1/1984 | Beysel et al. | |
| 4,449,990 A | 5/1984 | Tedford, Jr. | |
| 4,612,928 A | 9/1986 | Tiep et al. | |
| 4,627,860 A | 12/1986 | Rowland | |
| 4,673,415 A | 6/1987 | Stanford | |
| 4,765,804 A | 8/1988 | Lloyd-Williams et al. | |
| 4,869,733 A | 9/1989 | Stanford | |
| 5,060,514 A | 10/1991 | Aylsworth | |
| 5,071,453 A | 12/1991 | Hradek et al. | |
| 5,078,757 A | 1/1992 | Rottner et al. | |
| 5,144,945 A | 9/1992 | Nishino et al. | |
| 5,195,874 A | 3/1993 | Odagiri | |
| 5,248,320 A | 9/1993 | Garrett et al. | |
| 5,313,820 A | 5/1994 | Aylsworth | |
| 5,354,361 A | 10/1994 | Coffield | |
| 5,369,979 A | 12/1994 | Aylsworth et al. | |
| 5,405,249 A | 4/1995 | Benson | |
| 5,452,621 A | 9/1995 | Aylesworth et al. | |
| 5,474,595 A | 12/1995 | McCombs | |

(Continued)

FOREIGN PATENT DOCUMENTS

WO    WO 02/34368 A1    0/2002

OTHER PUBLICATIONS

European Search Report dated May 30th 2006.

(Continued)

*Primary Examiner*—Aaron J. Lewis
(74) *Attorney, Agent, or Firm*—Mark E. Scott; Conley Rose, PC

(57) ABSTRACT

A system for filling a portable cylinder with therapeutic gas, and providing therapeutic gas to a patient. Therapeutic gas delivery to a patient may be through a conserver, or may be in a continuous mode. Some embodiments of the invention may test the contents of the portable cylinder prior to filling. The specification also discloses a silent mode of operation where therapeutic gas is provided from the system by means of internal and/or external cylinders.

31 Claims, 3 Drawing Sheets

U.S. PATENT DOCUMENTS

| | | |
|---|---|---|
| 5,584,669 A | 12/1996 | Becker |
| 5,593,291 A | 1/1997 | Lynn |
| 5,603,315 A | 2/1997 | Sasso, Jr. |
| 5,746,806 A | 5/1998 | Aylsworth et al. |
| 5,858,062 A | 1/1999 | McCulloh et al. |
| 5,988,165 A | 11/1999 | Richey, II et al. |
| 6,302,107 B1 | 10/2001 | Richey, II et al. |
| 6,334,468 B1 | 1/2002 | Friestad |
| 6,342,090 B1 | 1/2002 | Cao |
| 6,393,802 B1 | 5/2002 | Bowser et al. |
| 6,394,088 B1 | 5/2002 | Frye et al. |
| 6,446,630 B1 | 9/2002 | Todd, Jr. |
| 6,651,653 B1 | 11/2003 | Honkonen et al. |
| 6,681,764 B1 | 1/2004 | Honkonen et al. |
| 6,698,423 B1 | 3/2004 | Honkonen et al. |
| 6,701,923 B1 | 3/2004 | Cazenave et al. |
| 6,742,517 B1 * | 6/2004 | Frye et al. ............. 128/201.21 |
| 6,805,122 B1 | 10/2004 | Richey, II et al. |
| 6,904,913 B1 * | 6/2005 | Aylsworth et al. ..... 128/204.22 |
| 6,910,510 B1 * | 6/2005 | Gale et al. .................... 141/82 |

OTHER PUBLICATIONS

Invacare Corporation, 510(K) No. K021685 Info, Summary, letter and division sign off, made public (decision date) Jul. 23, 2002, available on the US FDA website.

* cited by examiner

METHOD AND SYSTEM FOR DELIVERY OF THERAPEUTIC GAS TO A PATIENT AND FOR FILLING A CYLINDER

CROSS-REFERENCE TO RELATED APPLICATIONS

This application claims the benefit of provisional application Ser. No. 60/421,375 filed Oct. 24, 2002, and is also a continuation of application Ser. No. 10/636,055 filed Aug. 7, 2003 entitled, "Method and system for delivery of therapeutic gas to a patient and for filling a cylinder." now U.S. Pat. No. 6,904,913. Both of these applications are incorporated by reference as if reproduced in full below.

STATEMENT REGARDING FEDERALLY SPONSORED RESEARCH OR DEVELOPMENT

Not applicable.

BACKGROUND OF THE INVENTION

1. Field of the Invention

Embodiments of the present invention are directed to creation of therapeutic gas, possibly for delivery to a patient for respiratory use. More particularly, embodiments of the invention are directed to systems for creation of therapeutic gas for delivery to a patient and for filling portable cylinders for ambulatory use.

2. Background of the Invention

Many patients with lung and/or cardiovascular problems may be required to breathe therapeutic gas in order to obtain sufficient dissolved oxygen in their blood stream. So that these patients may be ambulatory, therapeutic gas may be delivered from a portable cylinder. A portable cylinder may, however, provide only limited volume, and therefore will periodically need to be refilled. While it is possible to have these cylinders exchanged or refilled by way of commercial home health care services, some patients have systems within their homes which perform a dual function: filling portable cylinders with oxygen therapeutic gas; and providing therapeutic gas to the patient for breathing. Systems such as these have come to be known as "trans-fill" systems.

U.S. Pat. No. 5,858,062 to McCulloh et al. (assigned to Litton Systems, Inc., and thus hereinafter the "Litton patent"), may disclose a system where atmospheric air may be applied to a pressure swing absorption (PSA) system which removes nitrogen from the air and thereby increases the oxygen content, e.g. to approximately 90% or above. In the Litton patent, oxygen-enriched gas exiting the PSA system may couple to a patient outlet and a pressure intensifier. The pressure of enriched gas supplied by the PSA system may be regulated (in this case lowered) before being provided to a patient. Likewise, the pressure of the enriched gas from the PSA system may be increased by the intensifier for filling the cylinder. Thus, in the Litton patent, the enriched gas product of the PSA system is separated into two streams (outlets in the terminology of the Litton patent) each having the same pressure. The Litton patent may also disclose the use of an oxygen sensor to monitor the enriched gas exiting the PSA system. However, the Litton patent discloses only monitoring oxygen content of the enriched gas exiting the PSA system, and situations where the oxygen content may be correct but the enriched gas product contains other harmful chemicals and/or gases may not be detected.

U.S. Pat. No. 6,393,802 to Bowser et al. (hereinafter the "Bowser patent") may disclose an oxygen concentrator that is adapted to supply therapeutic gas to the patient and/or to a cylinder filler, which cylinder filler is controlled to automatically fill a portable cylinder. Much like the Litton patent, the Bowser patent discloses an enriched gas product from an oxygen concentrator split into a first stream provided to a compressor (which may then be provided to fill a cylinder), and a second stream provided to a patient (possibly after proceeding through a flow regulator). The Bowser patent also discloses that prior to filling a cylinder, the gas pressure of the portable cylinder should be measured. If the gas pressure of the portable cylinder is below a predetermined safe minimum, the cylinder is not filled. The Bowser patent indicates this may be desirable because a cylinder having very little residual gas pressure may have been left open and the interior of the cylinder may have become contaminated.

U.S. Pat. No. 6,446,630 to Todd, Jr. (hereinafter the "Todd patent") may disclose a system where an enriched gas stream exiting an oxygen concentrator is selectively delivered to a patient (at least during a portion of the patient's inhalation) and the remainder of the time delivered to a cylinder filler. The Todd patent also mentions the use of an oxygen sensor to test the enriched gas from the oxygen concentrator provided to the patient, but fails to discuss the possibility that while oxygen concentration levels may be correct, other, harmful, gases may be present.

Thus, what is needed in the art is a method and related system that more closely monitors the therapeutic gas. Further, what is needed is a method and related system that more efficiently provides the therapeutic gas to a patient.

BRIEF SUMMARY OF SOME OF THE PREFERRED EMBODIMENTS

The problems noted above are solved in large part by a method and system for delivery of therapeutic gas to a patient and for filling of a cylinder. One exemplary embodiment may be a trans-fill system that comprises an intensifier (operable to increase pressure of therapeutic gas provided at an inlet of the intensifier to create a compressed therapeutic gas stream), a conserver coupled to the compressed therapeutic gas stream (operable to deliver a bolus of therapeutic gas during inhalation of the patient), a patient port coupled to the conserver (operable to provide the bolus of therapeutic gas to the patient), and a cylinder connector (operable to couple a portable cylinder to the compressed therapeutic gas stream). The trans-fill system itself may be operable to provide therapeutic gas to the cylinder connector to fill the portable cylinder while providing therapeutic gas to the patient through the conserver.

In other exemplary embodiments, contents of the connected cylinder may be tested prior to filling to determine whether impurities may be present. In some embodiments, if impurities are present, the connected cylinder may be evacuated, possibly by a compressor of an attached oxygen concentrator. In yet other embodiments, therapeutic gas delivered from a source such as an oxygen concentrator may be delivered in a continuous fashion to a patient by means of a flow meter. In these embodiments, the continuous flow setting of the flow meter may be sensed, and this sensed setting may be used to set bolus delivery through the conserver.

In yet other embodiments, additional therapeutic gas cylinders may be provided, and therapeutic gas may be provided to a patient by these additional cylinders without operating an oxygen concentrator and/or intensifier, and thus operation may be substantially silent.

The disclosed devices and methods comprise a combination of features and advantages which enable it to overcome the deficiencies of the prior art devices. The various characteristics described above, as well as other features, will be readily apparent to those skilled in the art upon reading the following detailed description, and by referring to the accompanying drawings.

BRIEF DESCRIPTION OF THE DRAWINGS

For a detailed description of the preferred embodiments of the invention, reference will now be made to the accompanying drawings in which.

NOTATION AND NOMENCLATURE

Certain terms are used throughout the following description and claims to refer to particular system components. This document does not intend to distinguish between components that differ in name but not function.

In the following discussion and in the claims, the terms "including" and "comprising" are used in an open-ended fashion, and thus should be interpreted to mean "including, but not limited to . . . ". Also, the term "couple" or "couples" is intended to mean either an indirect or direct connection. Thus, if a first device couples to a second device, that connection may be through a direct connection, or through an indirect connection via other devices and connections.

DETAILED DESCRIPTION OF THE PREFERRED EMBODIMENTS

Figure 1:
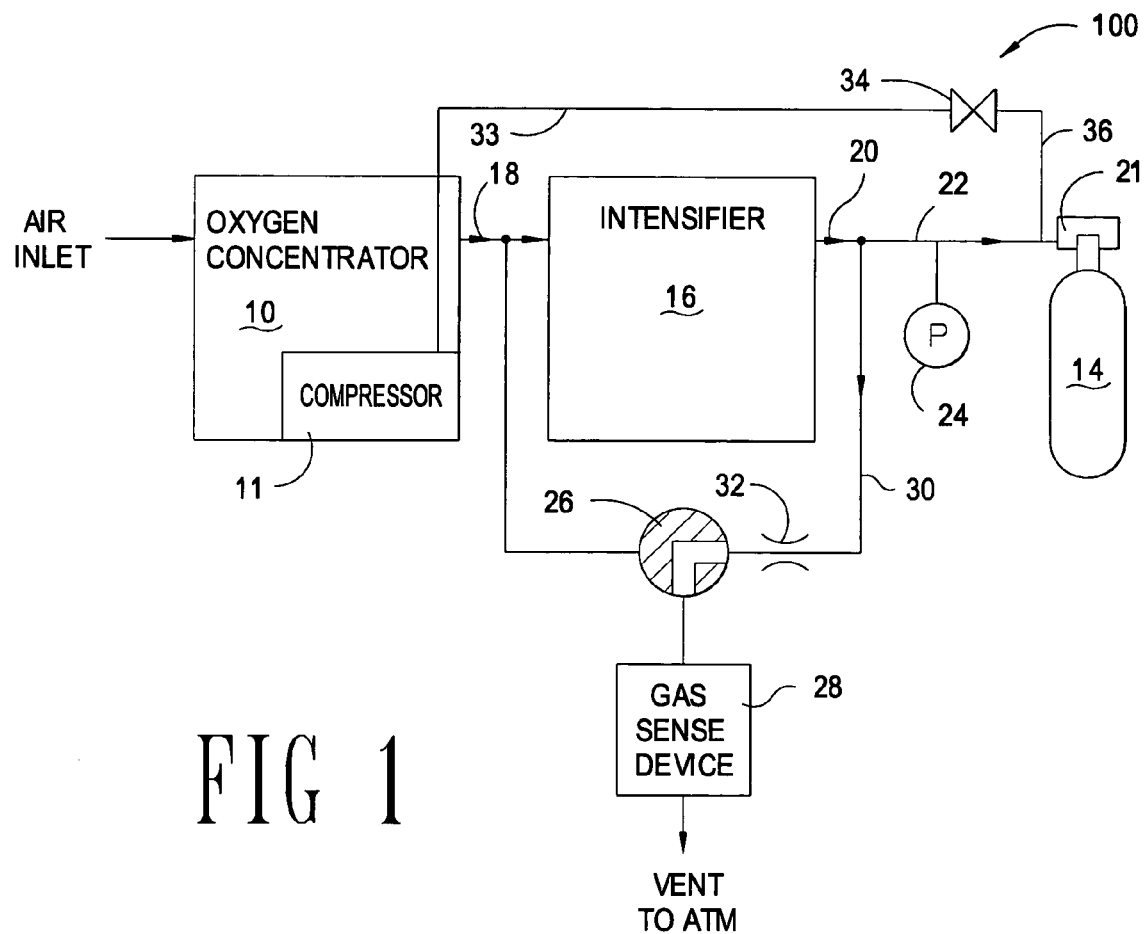
FIG. 1 illustrates a system for filling portable cylinders in accordance with at least some embodiments of the invention.

FIG. 1 illustrates a system for filling portable cylinders in accordance with at least some embodiments of the invention. Devices such as illustrated in FIG. 1 may be used, for example, in a patient's home to fill portable oxygen cylinders for ambulatory use. In particular, the system 100 may comprise an oxygen concentrator 10. The oxygen concentrator 10 may be any suitable device for increasing the oxygen content of therapeutic gas delivered to a patient. For example, the oxygen concentrator 10 may be a pressure swing absorption (PSA) system having a plurality of molecular sieve beds operated in a parallel relationship. Atmospheric air, possible drawn through the air inlet 12, may be drawn or pumped through a first molecular sieve bed where nitrogen molecules are trapped, and where oxygen and argon molecules flow through substantially unimpeded. By removing the nitrogen from atmospheric air, the concentration of oxygen in the gas exiting the sieve bed may be relatively high, e.g. 90% oxygen or more. Gas exiting a pressure swing absorption system may be referred to as oxygen-enriched gas or just enriched gas. The term therapeutic gas may encompass not only oxygen-enriched gas exiting a pressure swing absorption system, but also gas having a high therapeutic oxygen content from other sources, such as from liquid oxygen sources. While one molecular sieve bed acts to filter nitrogen, a second molecular sieve bed may use a portion of the therapeutic gas as a back-flow gas to flush trapped nitrogen to atmosphere, and prepare the bed for future operation. While a pressure swing absorption system may be the preferred system, any device or system capable of making or delivering therapeutic gas may be used.

For the preferred pressure swing absorption system, the pressure of the gas exiting the oxygen concentrator 10 may be on the order of 5–40 pounds per square inch (PSI). In order to force the therapeutic gas into a portable cylinder, for example portable cylinder 14, the pressure of the therapeutic gas may need to be increased. Thus, in some embodiments, therapeutic gas exiting the oxygen concentrator 10 may be supplied to an intensifier 16 by way of conduit 18. Intensifier 16 may be any device which is capable of taking the therapeutic gas at a first pressure and increasing the pressure. Intensifier 16 may be, in effect, a compressor of any available or after-developed type. The intensifier 16 increases the gas pressure to about 2200 PSI to create a compressed therapeutic gas system. The compressed therapeutic gas may flow into the cylinder 14 by way of conduits 20 and 22 and cylinder connector 21. Cylinder connector 21 may be any suitable device for coupling a portable cylinder to the system 100 or any of the systems discussed in this specification. The system 100 may stop operation when the portable cylinder 14 is full, possibly determined by a pressure transducer or pressure switch 24 coupled to conduit 22. Alternatively, the pressure switch 24 may couple directly to the portable cylinder 14.

Summarizing before continuing, a system 100 constructed in accordance with embodiments of the invention may draw air at atmospheric pressure into an oxygen concentrator 10. The oxygen concentrator 10 may enrich the oxygen content, possibly by removal of nitrogen. Therapeutic gas exiting the oxygen concentrator may be provided to an intensifier which increases the pressure, and the therapeutic gas at a higher pressure may be supplied to the portable cylinder 14.

Although portable cylinders that store therapeutic gas may normally contain a positive pressure, it is possible for contaminants to enter the portable cylinders. For example, a patient may leave a portable cylinder open, and when the pressure is exhausted contaminants may enter. Further, portable cylinders for delivery of therapeutic gas may be periodically cleaned, and the cleaning solution may remain as a contaminant. According to the related art teachings, if the pressure is below a preset threshold, for example 50 PSI, the cylinder should not be filled as it may be contaminated. However, contaminants within a cylinder may cause pressure. Thus, while testing the pressure within the cylinder prior to filling may provide some protection from contamination, in accordance with at least some embodiments of the invention the actual contents of the cylinder may be tested prior to filling the cylinder.

Still referring to FIG. 1, prior to attempting to fill the cylinder (and thus possibly before the oxygen concentrator 10 and intensifier 16 become operational), valve 26 may be positioned (possibly automatically) to place the gas sensing device or devices 28 in fluid communication with the portable cylinder 14. Pressure within the portable cylinder 14 causes gas to move through conduit 22, conduit 30, orifice 32, valve 26, and through the gas sensing device 28, where the gas may be tested.

Gas sensing device 28 may take many forms. In accordance with some embodiments of the invention, the gas sensing device 28 may be an oxygen-selective sensor, such sensors based on zirconium oxide, galvanic, or paramagnetic technologies. If the gas sensing device 28 is an oxygen-selective sensor, the device may analyze the actual percentage of oxygen in the gas. If the oxygen content of the gas falls below a preset threshold, e.g. 85% oxygen, this may be an indication that contaminants have entered or have been introduced into the portable cylinder 14.

In alternative embodiments of the invention, the gas sensing device 28 may be a time-of-flight density sensor. U.S. Pat. No. 5,060,514 teaches the use of time-of-flight sensors for measuring density, and thus purity, of a gas stream. Provisional Application Ser. No. 60/421,375, incorporated by reference above, also teaches a time-of-flight density sensor which may be used in accordance with embodiments of the invention. If the gas sense device 28 is a time-of-flight sensor, the density of the gas 14 may be indicative of whether contaminants are present in the portable cylinder 14.

While using an oxygen-selective sensor may provide an indication as to the percentage of oxygen in the gas, oxygen selective sensors may be unable to detect the type and presence of other, possibly harmful, gases. Likewise with respect to the time-of-flight density sensors, a density measurement standing alone may not be able to detect the presence of contaminants, particularly where those contaminants have density similar to the therapeutic gas. Thus, in some embodiments the gas sensing device 28 may be a combination of an oxygen-selective sensor and a density sensor. In these embodiments, if the oxygen-selective sensor determines that the oxygen content is above a predetermined level, such as 85% oxygen, and the density sensor determines that the density is within the range expected (the range expected for a high oxygen concentration in combination with mostly argon, as may be the enriched gas product from a pressure swing absorption system), then the portable cylinder 14 may be considered to be contamination free. This may be the case even if the initial pressure of the cylinder is below the preset limit previously used as an indication of contamination. If, on the other hand, the oxygen-selective sensor indicates that oxygen is within normal range, but the density sensor does not indicate a normal reading, this may be an indication that the argon normally present in oxygen-enriched gas may have been replaced with some other, possibly dangerous, gas. Likewise, if the oxygen sensor indicates that the oxygen concentration is below a predetermined threshold, the portable cylinder 14 may not be filled regardless of the density measurement results.

Thus, in accordance with at least some embodiments of the invention, the gas within the portable cylinder 14 may be sampled and analyzed to determine whether the portable cylinder 14 may be safely filled and used by a patient independent of its initial pressure.

In the event that a gas sensing device 28 determines prior to filling that the portable cylinder 14 is contaminated, in accordance with at least some embodiments of the invention, system 100 may evacuate the cylinder (pull a vacuum) to remove the contaminants. In particular, an oxygen concentrator 10 in the form of a pressure swing absorption system may comprise a compressor 11 that in one aspect compresses air to force it through a sieve bed, and the compressor may in a second aspect create a vacuum, possibly to remove nitrogen from a sieve bed that is not in operation. In the event that the cylinder 14 needs to be evacuated, the compressor 11 within the oxygen concentrator 10 may be utilized to evacuate the gases from the cylinder. In particular, the compressor 11 may couple to the oxygen cylinder 14 through conduit 33, valve 34, and conduit 36. The control system (not shown) may activate the compressor 11 and open valve 34 to apply vacuum to the portable cylinder 14. The steps of evacuating contaminants from the portable cylinder 14 may take many forms, and the precise mechanism may depend on the type of contamination. In some circumstances, simply pulling a vacuum to remove the free gases may be sufficient to remove the contaminants. In other situations, cyclic at least partial filling followed by evacuation may be necessary to flush the contaminants. After a sufficient number of cycles of at least partial filling and pulling a vacuum, the gas sensing device or devices 28 may determine that the contaminants have been removed, and the portable cylinder may be filled and used for ambulatory use.

In addition to sampling the gas within the portable cylinder 14 prior to filling, a system 100 in accordance with embodiments of the invention may also continuously, or periodically, sample gas produced by the oxygen concentrator 10 and/or intensifier 16. Consider a situation where an initial determination that the portable cylinder 14 is free of contaminants has been made, and the oxygen concentrator 10 and intensifier 16 are operational. By selective positioning of valve 26, the gas sense device 28 may sample the therapeutic gas exiting the oxygen concentrator 10. If at any time the gas sense device 28 determines that the therapeutic gas is below thresholds for purity and/or contains contaminants, a control system (not specifically shown) may cease production generation and sound an alarm. Likewise, the gas sense device 28 may sample the therapeutic gas as it exits the intensifier, again by selective placement of the valve 26.

Figure 2:
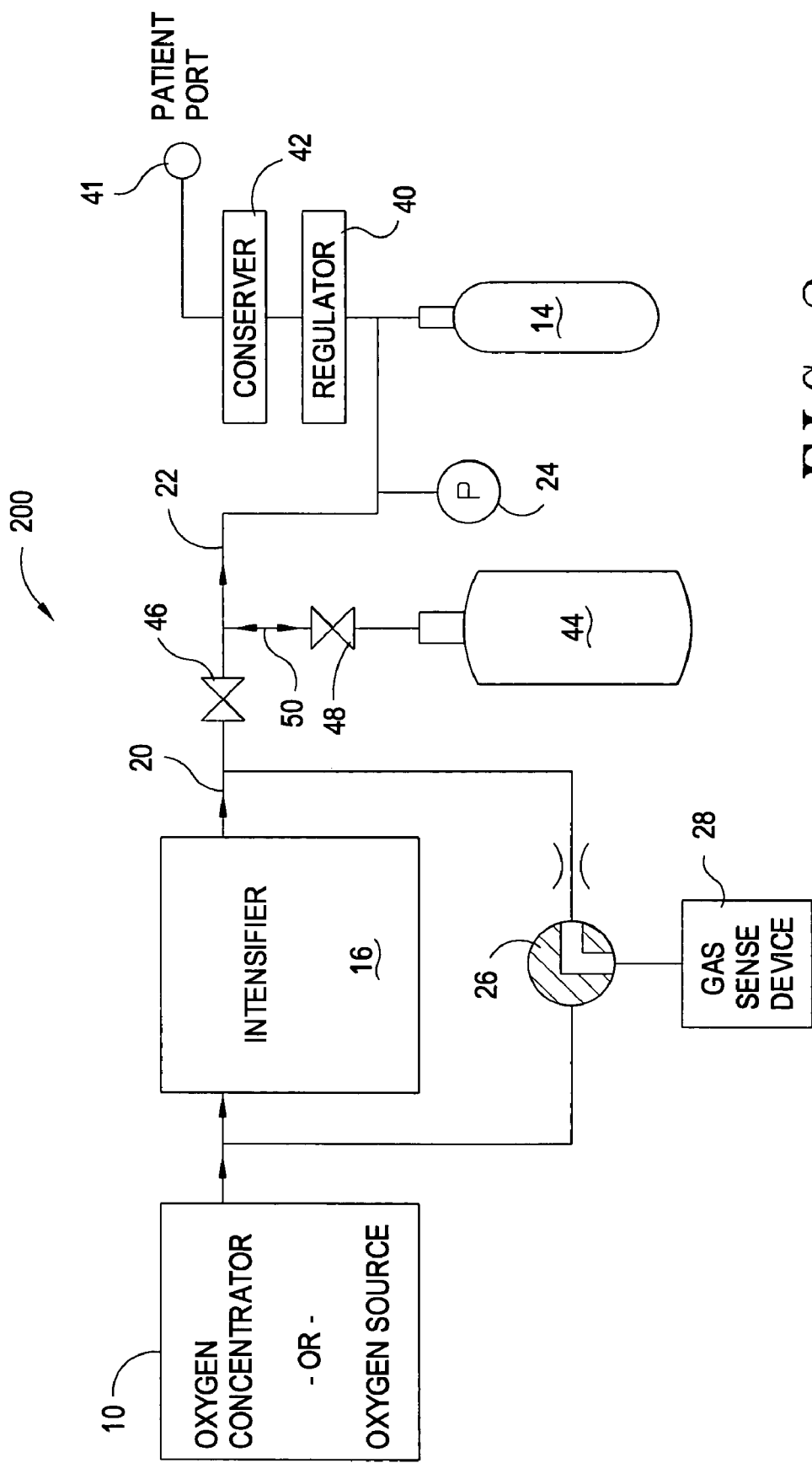
FIG. 2 illustrates a trans-fill system in accordance with at least some embodiments of the invention.

FIG. 2 illustrates a trans-fill system 200 in accordance with alternative embodiments of the invention. The trans-fill system 200 illustrated in FIG. 2 may produce therapeutic gas in a fashion similar to the system illustrated in FIG. 1. Trans-fill system 200 may be used in locations where a therapeutic gas source is available, e.g. in a hospital where oxygen may be provided in each room. In these circumstances, the oxygen concentrator may be omitted from the trans-fill system 200. Thus, trans-fill system 200 may optionally comprise an oxygen concentrator 10. The gas sense device 28 may check the portable cylinder 14 for contaminants prior to filling. Likewise, gas sense device 28 may check the purity of the therapeutic gas during normal operations. If the portable cylinder 14 is found to contain contaminants, or the therapeutic gas used for filling operations is found to be contaminated, the trans-fill system 200 may sound appropriate alarms and/or stop gas production and/or delivery. Trans-fill system 200 may also have the capability of evacuating the portable cylinder 14, although this ability is not specifically illustrated in FIG. 2 so as not to unduly complicate the drawing.

In the embodiments illustrated in FIG. 2, the oxygen concentrator 10 and intensifier 16 may provide therapeutic gas to fill cylinder 14, while at the same time a patient may be provided therapeutic gas. In particular, the portable cylinder 14 may have coupled thereto a regulator 40 which provides therapeutic gas from the portable cylinder at a pressure of between approximately 20–25 PSI. The therapeutic gas in the 20–25 PSI range may then be applied to a conserver 42, which may further regulate pressure of the therapeutic gas, and also senses or anticipates the inhalation cycle of the patient and provides a bolus of gas during the initial stages of the inhalation to the patient. U.S. Pat. No. 4,612,928 to Tiep et al. is exemplary of conserver technology which may be used in accordance with embodiments of the invention.

Each of the embodiments disclosed in FIGS. 1 and 2 may utilize an intensifier 16. As previously mentioned, the intensifier 16 may effectively be a compressor, possibly having air-actuated piston-type compression chambers. For this reason, the intensifier 16 may emit audible noise. Likewise, the compressor 11 of the oxygen concentrator 10 (if present) may emit audible noise. During daytime use when a patient is awake, the noise that an intensifier 16 and/or compressor 11 of the oxygen concentrator makes may not be a problem. However, during night-time use, a patient may be disturbed by the level of audible noise generated by the trans-fill system 200. To address potential audible noise problems, embodiments of the invention may have a substantially silent mode of operation, which may be used at night and at other times when therapeutic gas delivery is desired but where audible noise may present problems.

Referring again to FIG. 2 the trans-fill system 200 may optionally comprise a cylinder 44. Cylinder 44 may be internal or external to the trans-fill system 200, and may also comprise multiple internal or external cylinders or combinations of both. The cylinder 44 may be of greater volume than the portable cylinder 14. During operation, the combination oxygen concentrator 10 and intensifier 16 may fill the cylinder 44. Filling of the cylinder 44 may take place at the same time as filling the portable cylinder 14, may take place when the portable cylinder 14 is disconnected from the trans-fill system 200, and/or may take place while providing therapeutic gas to the patient through the regulator 40 and conserver 42. The cylinder 44 preferably has sufficient volume to supply therapeutic gas to the patient for several hours, e.g. overnight. Thus, during filling of the cylinder 44 (and possibly the portable cylinder 14) the oxygen concentrator 10 and intensifier 16 may provide compressed therapeutic gas to the conduit 20. The therapeutic gas may flow through the valve 46, and then into the cylinder 44 through the valve 48 and conduit 50. Valve 46 may alternatively be a check valve. If filling of cylinder 44 is not desired, valve 48 may be closed. At times when the patient desires a silent operation of the trans-fill system 200 (and when cylinder 44 has sufficient stored therapeutic gas), the oxygen concentrator 10 and intensifier 16 may be turned off, and valve 46 may be closed, thus allowing therapeutic gas within the cylinder 44 to flow through the valve 48 and conduit 50 and onto the patient port 41 by way of regulator 40 and conserver 42. In some embodiments, cylinder 44 and portable cylinder 14 may contribute to delivery of therapeutic gas during silent operation. As the pressure supplied to at least the regulator 40 starts to drop, indicating that the cylinder 44 and/or portable cylinder 14 may be approaching an empty condition, this pressure may be detected (e.g. by pressure switch 24), and the oxygen concentrator 10 and intensifier 16 started in order to resume delivery of therapeutic gas.

Much like the discussion above with respect to checking the contents of the portable cylinder 14, the gas sense device 28 may also analyze the gas of cylinder 44 prior to filling, and also periodically or continuously analyze the therapeutic gas during filling of the cylinder 44.

Having a cylinder 44 with a volume larger than that of the portable cylinder 14 also provides the capability for the trans-fill system 200 to have a quick-fill feature for the portable cylinder 14. Assume for purposes of explanation that valve 48 is closed and that the internal cylinder 44 is full or substantially full. To fill the portable cylinder 14, the patient may select that the oxygen concentrator and intensifier fill the portable cylinder 14. Filling using the therapeutic gas exiting the intensifier may be relatively slow, e.g. 2 liters per minute. The patient may also select a quick-fill, where the therapeutic gas provided to the cylinder 14 may come solely from the cylinder 44, or possibly from a combination of the oxygen concentrator and intensifier 16 and the cylinder 44. Operation under either of these two circumstances may provide for a faster fill of the portable cylinder 14 than may be achieved without the cylinder 44 contributing therapeutic gas.

Figure 3:
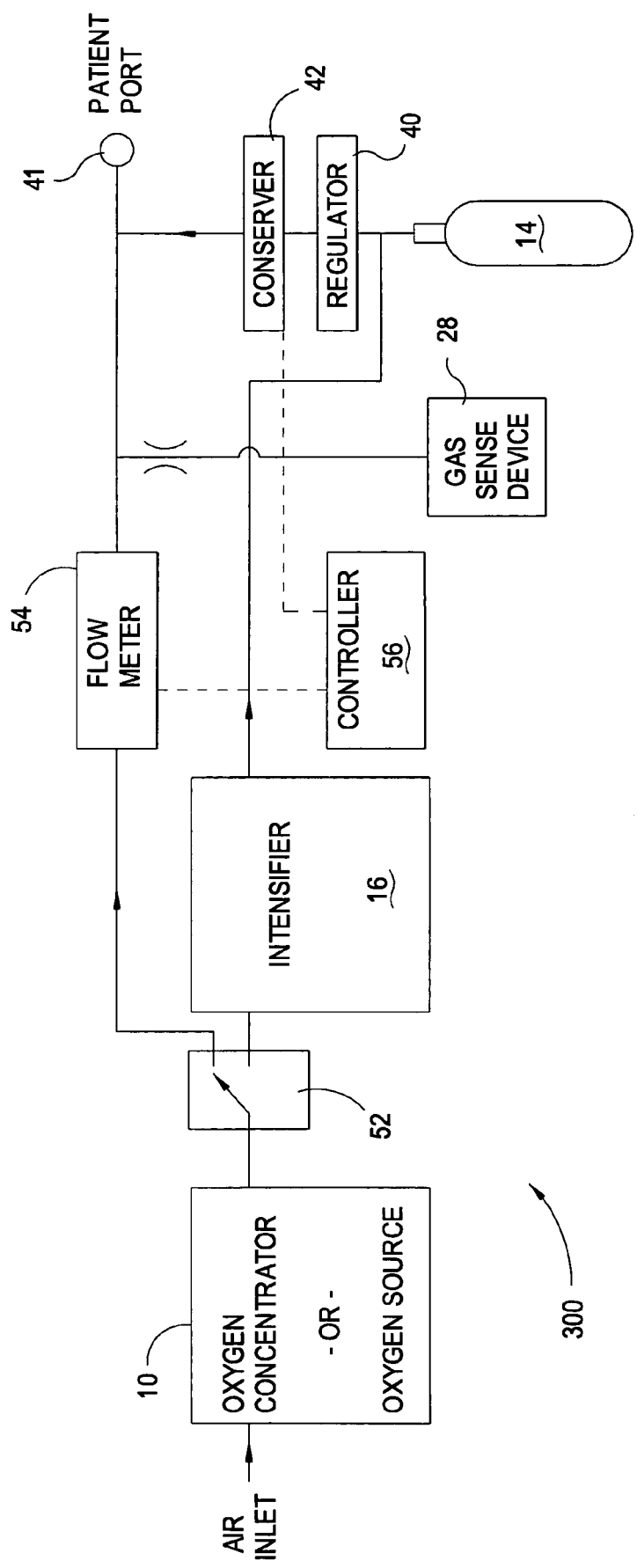
FIG. 3 illustrates a trans-fill system having a continuous delivery capability in accordance with at least some embodiments of the invention.

FIG. 3 illustrates another embodiment of the invention that may be capable of providing a continuous flow of therapeutic gas to the patient as an alternative to providing therapeutic gas from a conserver to the patient. In particular, the trans-fill system 300 illustrated in FIG. 3 may optionally comprise an oxygen concentrator or oxygen source 10. The oxygen concentrator may be coupled to the intensifier 16 by valve 52. With the valve 52 in a first position (not specifically shown in FIG. 3), therapeutic gas exiting the oxygen concentrator 10 may couple to the intensifier 16, where the pressure may be increased for being provided to the cylinder 14 and the regulator 40. In this mode of operation, and much like the discussion with respect to FIG. 2, therapeutic gas may be provided to the patient port 41 from the cylinder 14 and/or intensifier 16 through the regulator 40 and conserver 42. Although FIG. 3 does not illustrate an additional cylinder, such as cylinder 44 in FIG. 2, one may likewise be present. In a second mode of operation, the valve 52 may be adjusted such that the therapeutic gas exiting the oxygen concentrator 10 (or other oxygen source) may fluidly couple to a flow meter 54 (this valve position is illustrated in FIG. 3). In this mode, the intensifier 16 is not provided a stream of therapeutic gas. The flow meter 54 may take any suitable form, but in accordance with these embodiments of the invention the flow meter 54 may be a device by which the patient may selectively set a continuous flow of oxygen. For example, by turning a knob (not specifically shown) on the flow meter 54, the patient may select any of a range of possible continuous flows, e.g. half a liter per minute to five liters per minute. Turning the knob may vary size of an orifice in the therapeutic gas flow stream to provide the desired outlet volume. The regulated side of the flow meter 54 may thus couple to the patient by way of patient port 41.

Thus, embodiments such as illustrated in FIG. 3 may have two modes of operation: a continuous flow mode where the user may select the volume of flow; and a delivery through the conserver, which may provide a bolus of therapeutic gas during inhalation. Although it may be possible to independently set the continuous flow rate of the flow meter and the bolus delivery of the conserver 42, in accordance with at least some embodiments of the invention the continuous flow setting of the flow meter may be read by a controller 56. The controller 56, determining or sensing the desired continuous flow rate, may set the conserver flow based on the continuous flow. For example, the controller 56 may set the conserver to provide a 16.5 milli-liter bolus for every liter per minute of continuous flow set by the patient. Thus, for a 2 liter-per-minute continuous flow, the controller may set the conserver to deliver a 33 milli-liter bolus of therapeutic gas, possibly at the beginning of each inhalation. In this way, the patient may only need to make one flow setting.

Controller 56 may be any suitable control device, such as, but without limitation, a microcontroller program to perform the desired tasks, a microprocessor executing programs to perform the desired task, or possibly some other form of modular controller, such as a programmable logic controller (PLC). The controller 56 may electrically couple to both the flow meter 54 and conserver 42, as shown in dashed lines in FIG. 3. Although not specifically shown, the controller 56 may also electrically couple to the oxygen concentrator 10

(if present), intensifier 16, the pressure switch 24 (FIG. 2), and the gas sense device or devices 28. Additionally, controller 56 may couple to and control the position of various valves in the system, for example valve 26 (FIGS. 1 and 2), valve 34 (FIG. 1), valves 46 and 48 (FIG. 2), and valve 52 (FIG. 3). Thus, the controller 56 may control each of these devices for autonomous operation of the trans-fill system.

Figure 4:
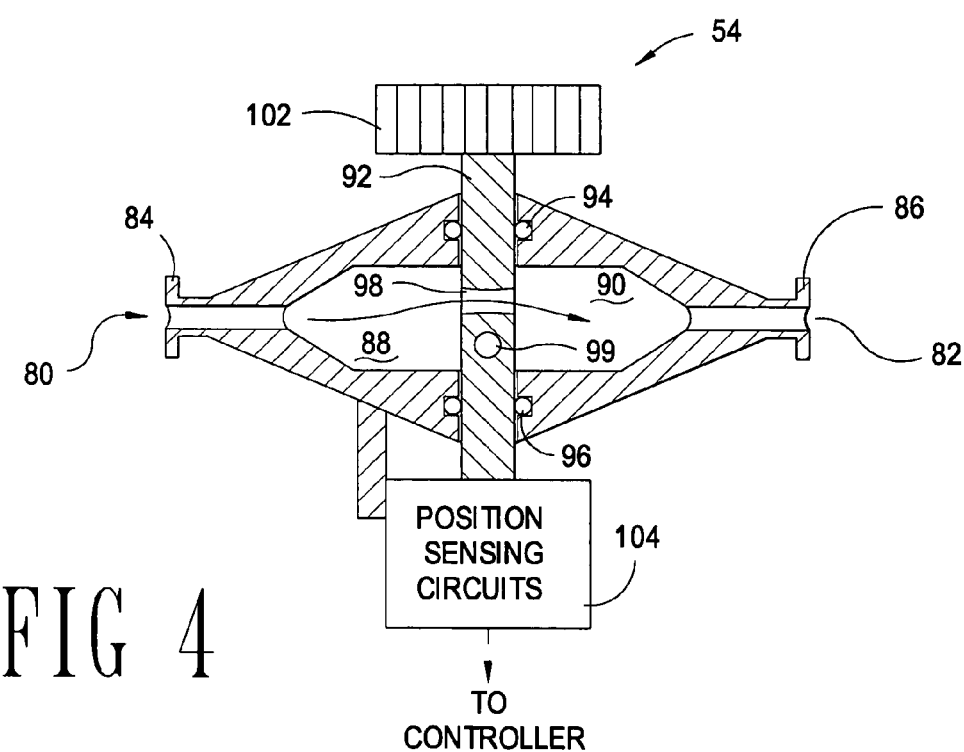
FIG. 4 illustrates a cross-sectional view of an exemplary flow meter constructed in accordance with at least some embodiments of the invention.

FIG. 4 illustrates a cross-sectional view of a flow meter 54 constructed in accordance with embodiments of the invention. In particular, flow meter 54 may have an inlet port 80 and an outlet port 82. Inlet port 80 may have a flange 84, and likewise outlet port 82 may have a flange 86. While FIG. 4 illustrates a flange on both the inlet 80 and outlet 82 ports, any suitable connecting mechanism may be used. Inlet port 80 may be fluidly coupled to inlet chamber 88. Likewise, outlet port 82 may be fluidly coupled to an outlet chamber 90. The inlet chamber 88 and outlet chamber 90 may be fluidly separated by a cylindrical shaft 92 extending through the body of the flow meter 54. Although not specifically shown, sealing between the inlet and outlet chambers by the cylindrical shaft 92 may be by way of gaskets, O-rings, or by close tolerances between the cylindrical shaft 92 and the body of the flow meter 54. Therapeutic gas within the inlet chamber 88 and outlet chamber 90 may be substantially prevented from escaping to atmosphere way of O-rings 94 and 96. In order to control the continuous flow of therapeutic gas through the flow meter 54, the cylindrical shaft 92 may have a plurality of holes or orifices therethrough of varying sizes. In particular, cylindrical shaft 92 may have a first orifice 98 and a second orifice 99. In the illustrated embodiment of FIG. 4, the axis of orifice 98 may be perpendicular to the axis of orifice 99; however, any number of orifices may be used, and the relationship of their axes need not be perpendicular. As illustrated in FIG. 4, orifice 98 is positioned to allow a continuous flow of therapeutic gas from the inlet chamber 88 to the outlet chamber 90. In the position illustrated in FIG. 4, either one or both of the inlet and the outlet of orifice 99 may be sealed against the body of the flow meter 54 (although the sealing is not specifically shown). In order to set a continuous flow of therapeutic gas, a patient may rotate knob 102. Rotation of knob 102 may, for example, place orifice 99 in such a position that therapeutic gas may flow therethrough. Orifice 99 may be of larger or smaller diameter, and thus provide a different flow of gas through the flow meter 54. Rotation of the knob 102 need not necessarily allow therapeutic gas to flow through only a single orifice. In some positions knob 102 may allow therapeutic gas to flow through both orifice 98 and 99. In this circumstance, the total continuous flow through the flow meter 54 will be the combination of the flow through the orifice 98 and the orifice 99. Although only two orifices 98, 99 are shown, any number of orifices may be used with varying diameters, and with varying angles between the axes such that turning knob 102 may allow therapeutic gas to flow through one or more of these orifices to control the continuous flow setting.

Cylindrical shaft 92 preferably also extends below the housing of the flow meter 54. A position-sensing circuit 104 may mechanically couple to the cylindrical shaft 92 and may be adapted to sense the radial position of the cylindrical shaft 92. In this way, the position-sensing circuit 104 may be able to determine the continuous gas flow setting of the flow meter 54. Position-sensing circuit 104 may take many forms. In some embodiments, the position-sensing circuit may be a rheostat or potentiometer whose resistance may be indicative of the radial position of the cylindrical shaft 92. In alternative embodiments, the sensing circuit 104 may be a plurality of microswitch devices in operational relationship to grooves or flat spots on the outer surface of the cylindrical shaft 92. By actuation of the switches when they come in operational relationship with the grooves or flat surfaces, the radial position of the cylindrical shaft 92 may be determined. Regardless of the precise mechanism by which the radial position of the cylindrical shaft 92 is made, this information may be coupled to the controller (FIG. 3), and the controller may set the bolus size for the conserver 42 using this information.

In the illustrative embodiments of FIG. 4, only the radial position of the cylindrical shaft 92 may place one or more orifices in the flow paths of the continuous flow through the flow meter 54. In alternative embodiments of the invention, the cylindrical shaft 92 may also translate vertically by turning of knob 102, and this vertical translation (possibly in combination with radial translation) may be the mechanism by which additional and/or varying size orifices may be placed within the flow stream. In these alternative embodiments, the position-sensing circuit may also sense the vertical position of the cylindrical shaft 92 by any suitable means.

FIG. 3 also illustrates that the gas sense device 28 need not necessarily couple as illustrated in FIGS. 1 and 2. In particular, the gas sense device 28 may be fluidly coupled to the therapeutic gas downstream of the flow meter 54, which coupling point is also downstream of the conserver 42. While it is possible for the gas sense device 28 to operate continuously, in accordance with at least some embodiments of the invention, the gas sense device 28, when sensing therapeutic gas provided by the oxygen concentrator 10 or exiting the intensifier 16, preferably samples the gas approximately every ten minutes. Operating the gas sense device 28 every ten minutes may extend the life of various components of the gas sense device 28, and in particular may extend the life of oxygen selective sensors such as the zirconium oxide technologies. With the gas sense device 28 coupled as illustrated in FIG. 3, while supplying therapeutic gas to the patient port 41 through conserver 42 there may be insufficient flow for analysis. Thus, in these embodiments the system 300 may either: momentarily switch to a continuous flow mode (by positioning of valve 42) to allow sufficient flow for the gas sense device 28 to operate; or by increasing the bolus size from conserver 42 for sufficient time to allow the gas sense device 28 to operate.

Although FIGS. 1–3 illustrate various embodiments of the invention, it should be noted that features of any of the embodiments not shown in the other figures may be utilized in those alternative embodiments. For example, the line 33 of FIG. 1 coupling the compressor 11 of oxygen concentrator 10 to the cylinder 14 may likewise be used in the embodiments illustrated in FIGS. 2 and 3. Further, the internal cylinder 44 illustrated in FIG. 2 may likewise be utilized in the embodiments illustrated in FIG. 3. Further still, gas sense device 28 may be fluidly coupled to the systems as illustrated in FIGS. 1 and 2, or alternatively in FIG. 3. Each of these variations fall within the scope and spirit of the invention.

Referring to all the figures generally, it should be understood that each of the valves may be directly or indirectly controlled by the controller 56, though the controller is not shown in all the figures so as not to unduly complicate the drawings. Thus, valve 26 of FIG. 1, which selects a source for testing by gas sense device 28 from the outlet side of the oxygen concentrator 10 or the outlet side of intensifier 16, may be controlled by the controller 56. Likewise, the valve 52 of FIG. 3, that selects operation in a continuous mode or allowing the therapeutic gas exiting the oxygen concentrator 10 to proceed at intensifier 16, may likewise be selectively positioned, directly or indirectly, by the controller 56. Valve 46, which may be closed during silent operation (and likewise valve 48, which may be open during silent operation), may be controlled by a controller 56.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. A method comprising:
    compressing a stream of low-pressure therapeutic gas to form a compressed therapeutic gas stream of sufficient pressure to fill a cylinder;
    providing a first portion of the compressed therapeutic gas stream to fill a cylinder; and concurrently
    providing a second portion of the compressed therapeutic gas stream to a patient as a bolus of therapeutic gas.

2. The method as defined in claim 1 further comprising, prior to compressing step and the providing steps, testing gas within the cylinder.

3. The method as defined in claim 2 wherein testing gas within the cylinder further comprises measuring the oxygen content of gas within die cylinder.

4. The method as defined in claim 2 wherein testing gas within the cylinder further comprises measuring the density of the gas within the cylinder.

5. The method as defined in claim 4 wherein testing the gas within the cylinder further comprises measuring the oxygen content of the gas within the cylinder.

6. The method as defined in claim 2 further comprising refraining from filling the cylinder if the gas within the cylinder contains contaminants.

7. The method as defined in claim 2 further comprising setting a volume of the bolus of therapeutic gas based on a sensed setting for a continuous flow of Therapeutic gas through a flow meter.

8. The method as defined in claim 1 further comprising, concurrently with the compressing, generating the stream of low-pressure therapeutic gas.

9. A system comprising;
    a compressor operable to increase pressure of therapeutic gas provided at an inlet of the compressor to create a compressed therapeutic gas stream of greater than 2000 pounds per square inch (PSI);
    a cylinder coupled to the compressed therapeutic gas stream; and
    a conserver coupled to the compressed Therapeutic gas stream, the conserver operable to deliver a bolus of therapeutic gas during inhalation of a patient;
    wherein the system is operable to provide therapeutic gas from the cylinder when the compressor is not in operation; and
    wherein the system is operable to provide Therapeutic gas to the cylinder while providing therapeutic gas to The patient through the conserver.

10. The system as defined in claim 9 further comprising an oxygen concentrator coupled to the compressor, the oxygen concentrator operable to provide therapeutic gas to The compressor.

11. The system as defined in claim 10 wherein the oxygen concentrator further comprises a pressure swing absorption system.

12. The system as defined in claim 9 further comprising a connector operable to selectively couple the cylinder to the system.

13. The system as defined in claim 12 wherein the cylinder is a portable cylinder.

14. The system as defined in claim 9 wherein the cylinder is internal to the system.

15. The system as defined in claim 14 further comprising a portable cylinder coupled to the compressed therapeutic gas stream, and wherein the system is operable to provide Therapeutic gas from the cylinder and the portable cylinder when the compressor is not in operation.

16. The system as defined in claim 9 wherein the compressor further comprises an intensifier.

17. An apparatus comprising:
    an intensifier operable to take therapeutic gas at a first pressure and increase the pressure of the therapeutic gas to a second pressure, higher than the first pressure;
    a fill port fluidly coupled to the therapeutic gas at the second pressure, the fill port operable to selectively couple a cylinder to he filled with therapeutic gas;
    a gas sense device coupled to the therapeutic gas at the second pressure, the gas sense device operable to detect content of gas within the cylinder prior to filling.

18. The apparatus as defined in claim 17 wherein the gas sense device further comprises an oxygen-specific sensor.

19. The apparatus as defined in claim 17 wherein the gas sense device further comprises a density sensor.

20. The apparatus as defined in claim 19 wherein the gas sense device further comprises an oxygen-specific sensor.

21. A trans-fill system comprising:
    a compressor operable to increase pressure of therapeutic gas to create a compressed therapeutic gas stream having sufficient pressure to fill a cylinder;
    a conserver coupled to the compressed therapeutic gas stream, the conserver operable to deliver a bolus of therapeutic gas during inhalation of a patient; and
    a cylinder connector operable to couple a portable cylinder to the compressed therapeutic gas stream;
    wherein the trans-fill system is operable to provide therapeutic gas to the cylinder connector to fill the portable cylinder while providing therapeutic gas to the patient through the conserver.

22. The trans-fill system as defined in claim 21 wherein the pressure of the compressed therapeutic gas stream is above 40 PSI.

23. The trans-fill system as defined in claim 22 wherein the pressure of the compressed therapeutic gas stream is approximately 2200 PSI.

24. A trans-fill system comprising:
    an oxygen concentrator comprising a first compressor that creates therapeutic gas;
    a second compressor fluidly coupled to the oxygen concentrator that increases pressure of therapeutic gas to create a compressed therapeutic gas stream;
    a conserver coupled to the compressed therapeutic gas stream, the conserver operable to deliver a bolus of therapeutic gas during inhalation of a patient; and
    a cylinder connector operable to couple a portable cylinder to the compressed therapeutic gas stream;
    wherein the trans-fill system is operable to provide therapeutic gas to the cylinder connector to fill the portable cylinder while providing therapeutic gas to the patient through the conserver.

25. The trans-fill system as defined in claim 24 further comprising:

a gas sense device fluidly coupled to die cylinder connector, the gas sense device operable to detect purity of therapeutic gas; and wherein the trans-fill system is operable to allow a portion of the gas within a connected portable cylinder to flow to the gas sense device, and wherein the trans-fill system refrains from filling the connected portable cylinder if the purity of the gas in the bottle, as determined by the gas sense device, falls below a predetermined threshold.

26. A system comprising:

a compressor operable to increase pressure of oxygen-enriched gas provided at an inlet of the compressor to create a compressed therapeutic gas stream;

a portable cylinder fill port coupled to the compressed therapeutic gas stream; and an internal cylinder coupled to the compressed therapeutic gas stream and the cylinder fill port, wherein the internal cylinder has sufficient volume to fill a portable cylinder;

wherein the system is operable to fill the portable cylinder, at least in part, from therapeutic gas from the internal cylinder.

27. The system as defined in claim 26 wherein the system is operable to fill the portable cylinder with therapeutic gas from the internal cylinder when the compressor is not in operation.

28. The system as defined in clam 26 further comprising a conserver coupled to the compressed therapeutic gas stream, the conserver operable to deliver a bolus of therapeutic gas during inhalation of a patient, wherein the system is operable to provide therapeutic gas to the internal cylinder while providing therapeutic gas to the patient through the conserver.

29. The trans-fill system as defined in claim 21 further comprising an oxygen source fluidly coupled to the compressor, wherein the oxygen source is operable to provide therapeutic gas to the compressor.

30. A system comprising:

a compressor operable to increase pressure of therapeutic gas provided at an inlet of the compressor to create compressed therapeutic gas of greater than 2000 pounds per square inch (PSI);

a cylinder fluidly coupled to the compressed therapeutic gas; and a conserver fluidly coupled to the compressed therapeutic gas, the conserver operable to deliver a bolus of therapeutic gas during inhalation of a patient;

wherein the system is operable to provide therapeutic gas from the cylinder when the compressor is not in operation; and wherein the system is operable to provide therapeutic gas to the cylinder while providing therapeutic gas to the patient through the conserver.

31. The system as defined in claim 30 wherein the cylinder is a portable cylinder.

* * * * *